United States Patent
Kajiro et al.

(10) Patent No.: US 7,491,921 B2
(45) Date of Patent: Feb. 17, 2009

(54) APPARATUS FOR OBSERVING PROTEIN CRYSTALS

(75) Inventors: Yoichi Kajiro, Tokyo (JP); Thomas Jay Friedlander, Rye Brook, NY (US)

(73) Assignee: Hirox Co., Ltd., Tokyo (JP)

( * ) Notice: Subject to any disclaimer, the term of this patent is extended or adjusted under 35 U.S.C. 154(b) by 520 days.

(21) Appl. No.: 11/371,297

(22) Filed: Mar. 8, 2006

(65) Prior Publication Data

US 2007/0217007 A1 Sep. 20, 2007

(51) Int. Cl.
  *G02B 27/22* (2006.01)
  *G01N 21/01* (2006.01)
  *H04N 7/18* (2006.01)
(52) U.S. Cl. ............... 250/208.1; 359/368; 348/79
(58) Field of Classification Search ............... 250/208.1; 359/368; 348/79
  See application file for complete search history.

(56) References Cited

U.S. PATENT DOCUMENTS 5,515,157 A * 5/1996 Can ............... 356/30
2004/0264765 A1 * 12/2004 Ohba ............... 382/154
2007/0217007 A1 * 9/2007 Kajiro et al. ............... 359/463

* cited by examiner

*Primary Examiner*—John R Lee
(74) *Attorney, Agent, or Firm*—McGlew & Tuttle, P.C.

(57) ABSTRACT

An apparatus for efficiently observing protein crystals for use in X-ray analysis is provided. This apparatus includes an ultra-compact proximity imaging unit and a three-dimensional observation adaptor (4) attached thereto. The imaging unit includes a CCD camera (2) and a lens system (3) and an illumination system in front of the CCD camera (2). The lens system (3) includes a variable or fixed magnification lens. The three-dimensional observation adaptor (4) has an optical-axis reflective surface (4c) disposed between the frontmost lens of the lens system (3) and a production container (100) containing protein crystals in the optical axis a of the lens system (3) and a revolving reflective surface (4d) disposed opposite the optical-axis reflective surface (4c) revolvably about the optical axis to three-dimensionally observe the crystals contained in the production container (100) in an oblique or lateral direction.

8 Claims, 5 Drawing Sheets

APPARATUS FOR OBSERVING PROTEIN CRYSTALS

BACKGROUND OF THE INVENTION

1. Field of the Invention

The present invention relates to apparatuses for observing protein crystals contained in a solution to discover high-quality protein crystals suitable for X-ray analysis. Specifically, the present invention relates to an apparatus for observing protein crystals suspended in a solution from around and/or along an optical axis in the form of a three-dimensional image to efficiently discover high-quality crystals suitable for X-ray analysis and thereby enhance the efficiency of X-ray analysis.

2. Description of the Related Art

Development of genetic drugs involves the production and X-ray analysis of protein crystals. Currently, however, high-quality crystals suitable for X-ray analysis are difficult to produce for several reasons. In a known process for observing protein crystals, screening and setting steps are repeated until high-quality crystals are discovered. This process takes much time and effort.

For known observation apparatuses, particularly, an image of crystals produced in a solution is taken with a CCD camera along the optical axis of a lens system and is processed with a computer. The resultant image, therefore, is a two-dimensional image of the crystals (in a production container) viewed perpendicularly. High-quality crystals may be invisible in this image because the crystals can overlap each other or can be hidden behind sediment. In that case, high-quality crystals are difficult to discover or may be determined to be unsuitable. The known system thus decreases the probability of discovering high-quality crystals, contributing to an increased number of screening and setting steps.

SUMMARY OF THE INVENTION

An object of the present invention is to provide an apparatus for observing protein crystals produced in a solution to efficiently discover high-quality crystals.

To achieve the above object, an apparatus for observing protein crystals for use in X-ray analysis according to the invention includes an ultra-compact proximity imaging unit and a three-dimensional observation adaptor attached thereto.

The imaging unit includes a CCD camera and a lens system and an illumination system in front of the CCD camera. The lens system includes a variable or fixed magnification lens having any optical magnification. The three-dimensional observation adaptor has an optical-axis reflective surface disposed between the frontmost lens of the lens system and a production container containing protein crystals in the optical axis of the lens system and a revolving reflective surface disposed opposite the optical-axis reflective surface revolvably about the optical axis to three-dimensionally observe the crystals contained in the production container in an oblique or lateral direction.

This apparatus allows efficient discovery of high-quality protein crystals.

In the apparatus for observing protein crystals for use in X-ray analysis according to one aspect of the invention, the three-dimensional observation adaptor includes a rotating ring rotatably attached to a body tube of the lens system and having the revolving reflective surface. The apparatus further includes a drive motor for freely controlling the rotation angle of the rotating ring to select any direction in which the crystals are observed with the revolving reflective surface through 360°.

In the apparatus for observing protein crystals for use in X-ray analysis according to another aspect of the invention, the three-dimensional observation adaptor is detachably attached to an end of a body tube of the lens system.

This apparatus allows two-dimensional observation as well as three-dimensional observation by detaching the three-dimensional observation adaptor.

In the apparatus for observing protein crystals for use in X-ray analysis according to another aspect of the invention, the optical-axis reflective surface and the revolving reflective surface have synchronously adjustable reflection angles.

This apparatus provides a wide range of observation angles.

OPERATION

Protein crystals are produced by bringing a protein-containing sample into contact with a protein-crystallization solution in a container.

Because the protein crystals thus produced include very few crystals suitable for X-ray analysis, only high-quality crystals must be selected from the large number of crystals suspended in the solution. In the present invention, the container is placed in the optical axis of the lens system and is three-dimensionally observed via the revolving reflective surface and the optical-axis reflective surface to discover high-quality crystals suitable for X-ray analysis. The angles of the two reflective surfaces may be changed in synchronization to perform the observation at any angle. This allows various observations of the crystals.

The crystals are viewed with a monitor by inputting images from the CCD camera into a computer. The crystals are observed in different directions by changing the position of the revolving reflective surface. The resultant data is used to display or record the quality, irregularity, and size, for example, of the crystals in digital form. This allows easy, efficient selection of crystals best suited to X-ray analysis.

The apparatus according to the present invention, as described above, enables three-dimensional observation of protein crystals in addition to conventional two-dimensional observation. The apparatus therefore not only allows the discovery of crystals overlapping each other or hidden behind sediment in a solution, but also allows the observation of the irregularity and size of crystals. Using the apparatus, high-quality crystals suitable for X-ray analysis can be efficiently discovered with fewer screening and setting steps.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
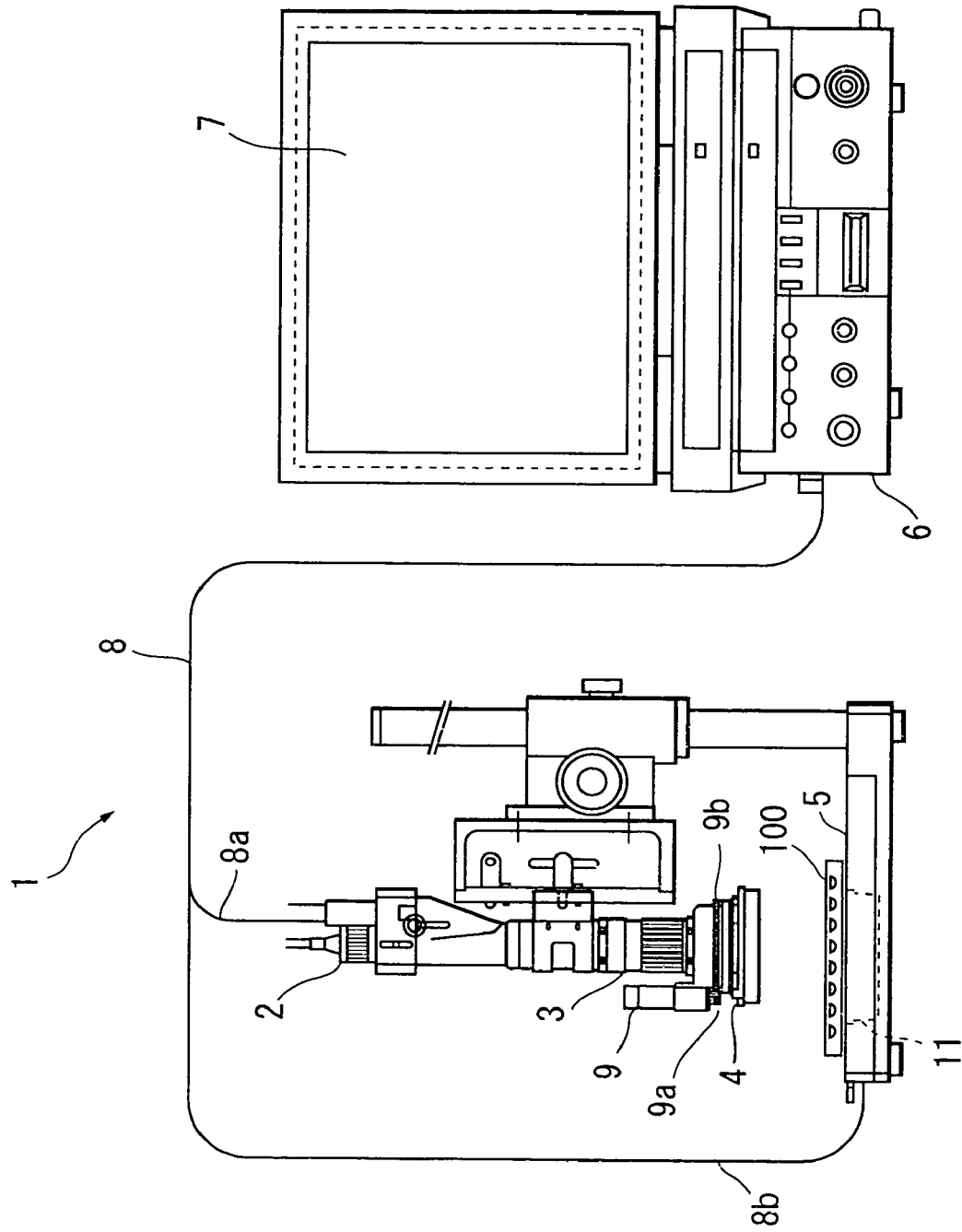
FIG. 1 is an overall view of an apparatus for observing protein crystals for use in X-ray analysis according to the present invention.
Figure 2:
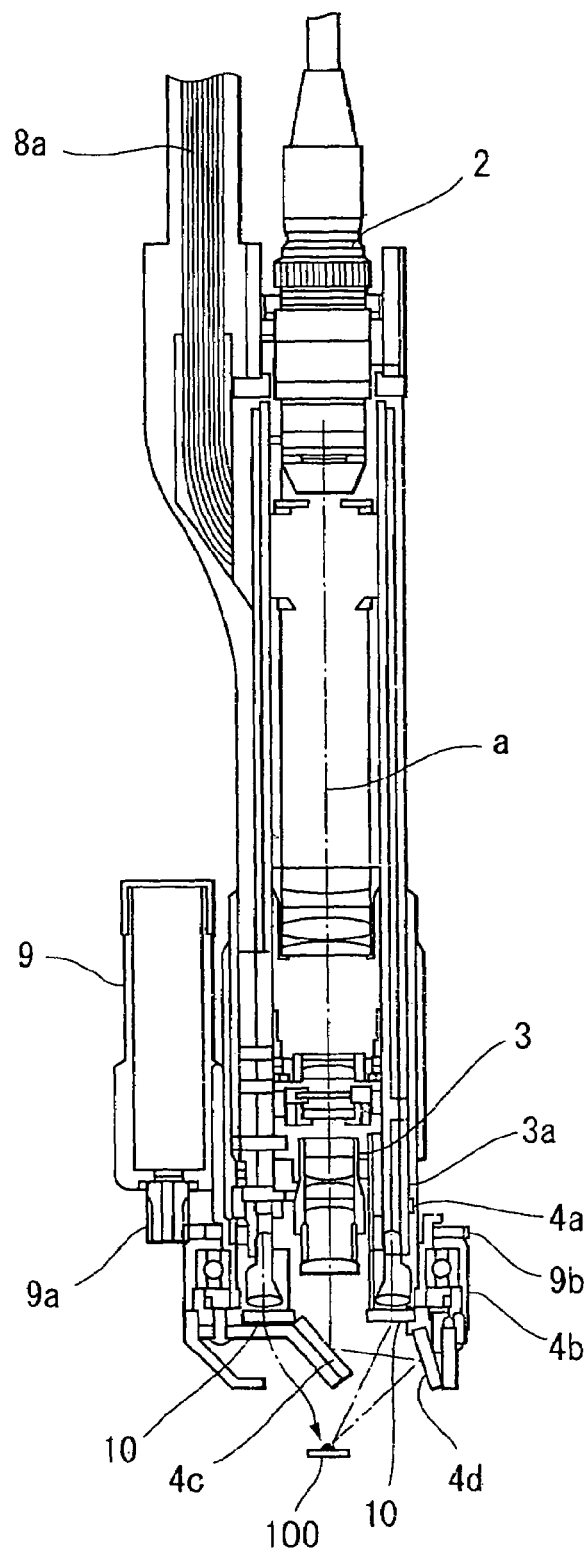
FIG. 2 is a diagram view of a CCD camera, a variable magnification lens system disposed in front of the CCD camera, and a three-dimensional observation adaptor attached to the front of the lens system.
Figure 3:
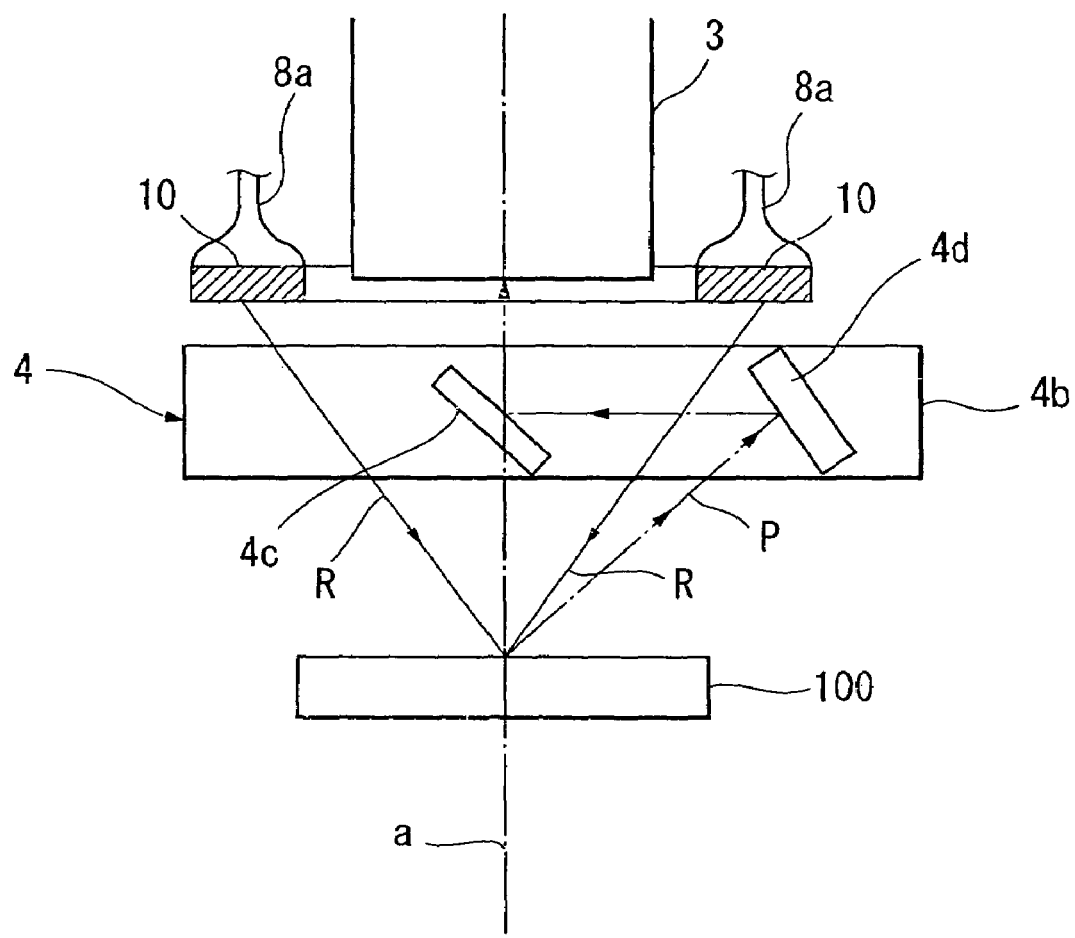
FIG. 3 is a partially sectional schematic diagram view of the three-dimensional observation adaptor.
Figure 4A:
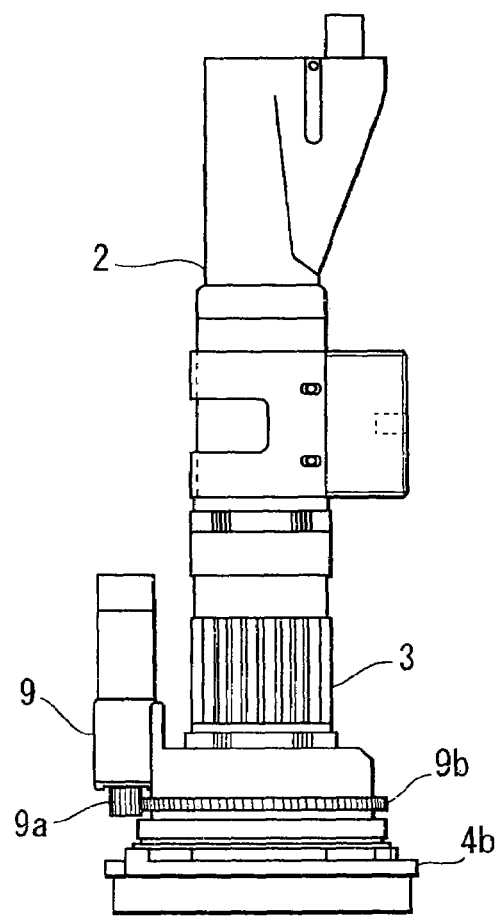
FIG. 4A is a diagram view of the CCD camera, the lens system, and the three-dimensional observation adaptor.
Figure 4B:
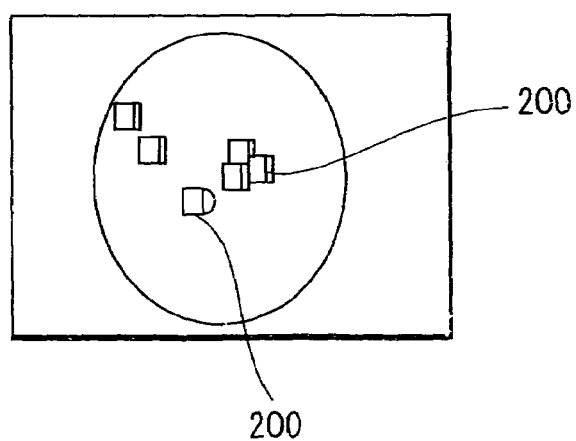
FIG. 4B is a diagram view of an image of protein crystals observed in three dimensions.
Figure 5:
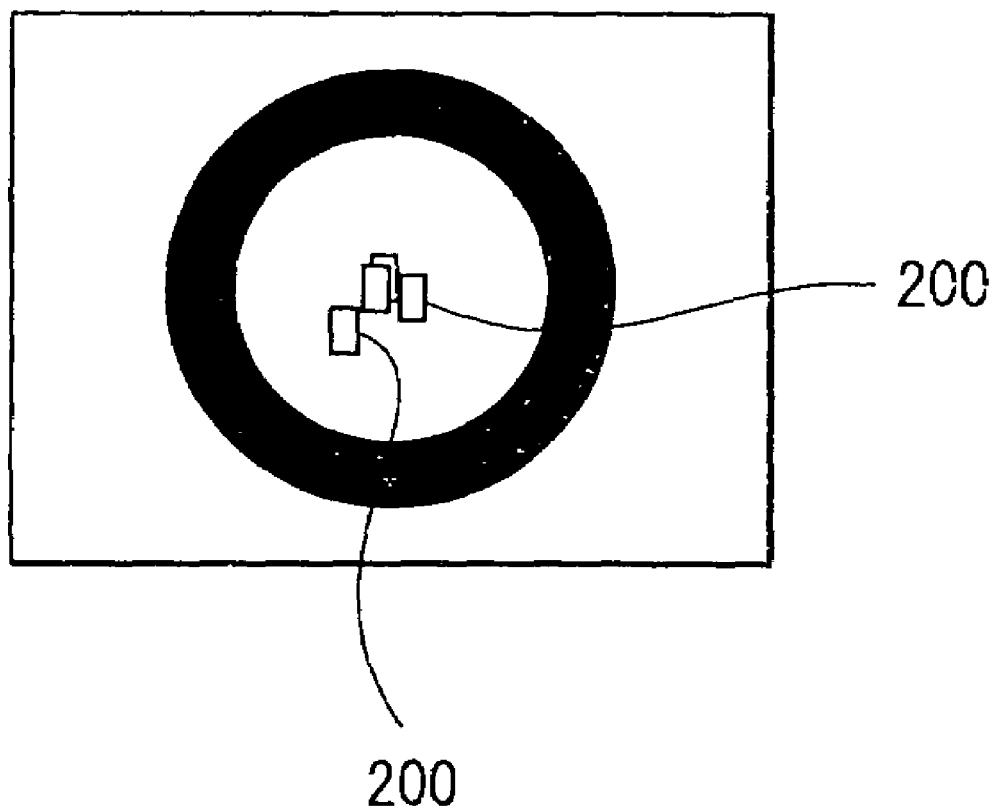
FIG. 5 is a diagram of an image of protein crystals directly observed.

Referring to the drawings in particular, an embodiment of the present invention 3 will now be described in detail with reference to FIGS. 1 to 6. FIG. 1 shows an overall view of an observation apparatus 1. FIG. 2 shows a diagram of a CCD camera, a lens system, and a three-dimensional observation adaptor. FIG. 3 shows a diagram of the three-dimensional observation adaptor. FIG. 4A presents a diagram of the CCD camera, the lens system, and the three-dimensional observation adaptor. FIG. 4B presents a diagram of an image of crystals observed in three dimensions. FIG. 5 shows a diagram of an image of crystals observed in two dimensions.

The observation apparatus 1 includes a CCD camera 2, a variable magnification lens system 3 disposed in front of the CCD camera 2, a three-dimensional observation adaptor 4 attached to an end of the lens system 3, a table 5 for supporting a crystal production container 100 below the lens system 3, a CCD camera controller 6, a monitor 7, a fiber-optic cable 8, a branch cable 8a connecting to the three-dimensional observation adaptor 4, and another branch cable 8b for illuminating the production container 100 from below.

The observation apparatus 1 is described below in more detail. Referring to FIGS. 2 and 3, the three-dimensional observation adaptor 4 is detachably attached to an end of a body tube 3a of the lens system 3. This observation adaptor 4 includes an adaptor body 4a for attachment, a rotating ring 4b rotatably attached to the front of the adaptor body 4a, an optical-axis reflective surface 4c disposed in the center of the rotating ring 4b so as to face outward with respect to an optical axis a, and a revolving reflective surface 4d disposed opposite the optical-axis reflective surface 4c in the rotating ring 4b so as to face the production container 100. Although the angles of the optical-axis reflective surface 4c and the revolving reflective surface 4d are fixed in this embodiment, the two reflective surface 4c and 4d may be disposed in the rotating ring 4b so that the reflection angles thereof can be controlled in synchronization for multi-angle observation. The reflection angles may be controlled in synchronization with, for example, a stepping motor.

A drive motor 9 is attached to the body tube 3a. The drive motor 9 has an output gear 9a meshing with a driven gear 9b disposed around the rotating ring 4b of the three-dimensional observation adaptor 4. As the drive motor 9 rotates the rotating ring 4b, the optical-axis reflective surface 4c rotates about the optical axis a of the lens system 3 together with the revolving reflective surface 4d. While the two reflective surfaces 4c and 4d rotate about the production container 100 on the container table 5, the CCD camera 2 takes three-dimensional images in different directions. These images can be observed with the monitor 7. In FIG. 3, reference letter P denotes incident light, and reference letter R denotes illumination light.

An annular illumination lens 10 is attached to the body tube 3a to illuminate the production container 100 from above with illumination light transmitted from a light source (not shown) through the fiber-optic cable 8 and the branch cable 8a. An illumination unit 11 is disposed on the table 5 side to illuminate the production container 100 with light from the branch cable 8b.

FIG. 4B shows an image of crystals observed in three dimensions using the observation apparatus 1.

This image separately shows crystals 200 in three dimensions to allow clear observation of the overall shapes of the crystals 200, including the shapes of irregularities. As a result, all crystals 200 in the production container 100 can be observed from therearound, including those overlapping each other and thus difficult to observe using known apparatuses. The observation apparatus 1 therefore allows the discovery of high-quality crystals suitable for X-ray analysis with fewer screening and setting steps.

FIG. 5 is a diagram of an image of crystals directly viewed with the three-dimensional observation adaptor 4 detached from the end of the body tube 3a.

While specific embodiments of the invention have been shown and described in detail to illustrate the application of the principles of the invention, it will be understood that the invention may be embodied otherwise without departing from such principles.

What is claimed is:

1. An apparatus for observing protein crystals for use in X-ray analysis, the apparatus comprising:
    an ultra-compact proximity imaging unit including a CCD camera and a lens system and an illumination system in front of the CCD camera, the lens system including a variable or fixed magnification lens having any optical magnification; and
    a three-dimensional observation adaptor attached to the imaging unit, said three-dimensional observation adaptor having an optical-axis reflective surface disposed between the frontmost lens of the lens system and a production container containing protein crystals in the optical axis of the lens system and a revolving reflective surface disposed opposite the optical-axis reflective surface revolvably about the optical axis to three-dimensionally observe the crystals contained in the production container in an oblique or lateral direction.

2. The apparatus for observing protein crystals for use in X-ray analysis according to claim 1, wherein the three-dimensional observation adaptor includes a rotating ring rotatably attached to a body tube of the lens system and having the revolving reflective surface, the apparatus further comprising a drive motor for freely controlling the rotation angle of the rotating ring to select any direction in which the crystals are observed with the revolving reflective surface through 360°.

3. The apparatus for observing protein crystals for use in X-ray analysis according to claim 1, wherein the three-dimensional observation adaptor is detachably attached to an end of a body tube of the lens system.

4. The apparatus for observing protein crystals for use in X-ray analysis according to claim 1, wherein the optical-axis reflective surface and the revolving reflective surface have synchronously adjustable reflection angles.

5. An apparatus for observing protein crystals for use in X-ray analysis, the apparatus comprising:
    a CCD camera;
    a lens system including a magnification lens;
    an illumination system operatively positioned relative to said CCD camera to illuminate a production container containing protein crystals disposed in an optical axis of the lens system; and
    a three-dimensional observation adaptor having an optical-axis reflective surface disposed between a frontmost lens of said lens system and the production container containing the protein crystals and having a revolving reflective surface disposed opposite the optical-axis reflective surface revolvably about the optical axis to three-dimensionally observe the crystals contained in the production container in an oblique or lateral direction.

6. The apparatus according to claim 5, wherein the three-dimensional observation adaptor includes a rotating ring rotatably attached to a body tube of the lens system and having said revolving reflective surface, the apparatus further comprising a drive motor for freely controlling the rotation angle of the rotating ring to select any direction in which the crystals are observed with the revolving reflective surface through 360°.

7. The apparatus according to claim 5, wherein said three-dimensional observation adaptor is detachably attached to an end of a body tube of said lens system.

8. The apparatus according to claim 5, wherein said optical-axis reflective surface and the revolving reflective surface have synchronously adjustable reflection angles.

* * * * *